United States Patent [19]

Birjukov et al.

[11] 4,198,866

[45] Apr. 22, 1980

[54] METHOD AND DEVICE FOR ULTRASONIC INSPECTION OF MATERIALS

[75] Inventors: Sergei B. Birjukov; Valery S. Gavrev; Jury M. Goncharuk; Alexandr V. Savitsky; Viktor A. Lonchak, all of Kishinev, U.S.S.R.

[73] Assignee: Vsesojuzny Nauchno-Issledovatelsky Institut Po Razrabotke Nerazrushajuschikh Metodov I Sredstv Knotrolya Kachestva Materialov"VNIINK", Kishinev, U.S.S.R.

[21] Appl. No.: 940,493

[22] Filed: Sep. 7, 1978

[51] Int. Cl.² .......................................... G01N 29/04
[52] U.S. Cl. ..................................................... 73/613
[58] Field of Search ................. 73/613, 609, 610, 611, 73/612, 614, 615

[56] References Cited

U.S. PATENT DOCUMENTS

| 3,404,560 | 10/1968 | Kaule ...................................... 73/613 |
| 3,690,156 | 9/1972 | Robinson .............................. 73/613 |

*Primary Examiner*—Stephen A. Kreitman
*Attorney, Agent, or Firm*—Haseltine, Lake & Waters

[57] ABSTRACT

A method for ultrasonic inspection of materials in which a reception and processing of ultrasonic vibrations reflected from a material being inspected is followed by separating signals from noise at a level that for each period of radiating ultrasonic vibrations is automatically set to be equal to the mean noise power per interval of time selected within the maximum sensitivity zone of a preceding period of radiating ultrasonic vibrations.

6 Claims, 14 Drawing Figures

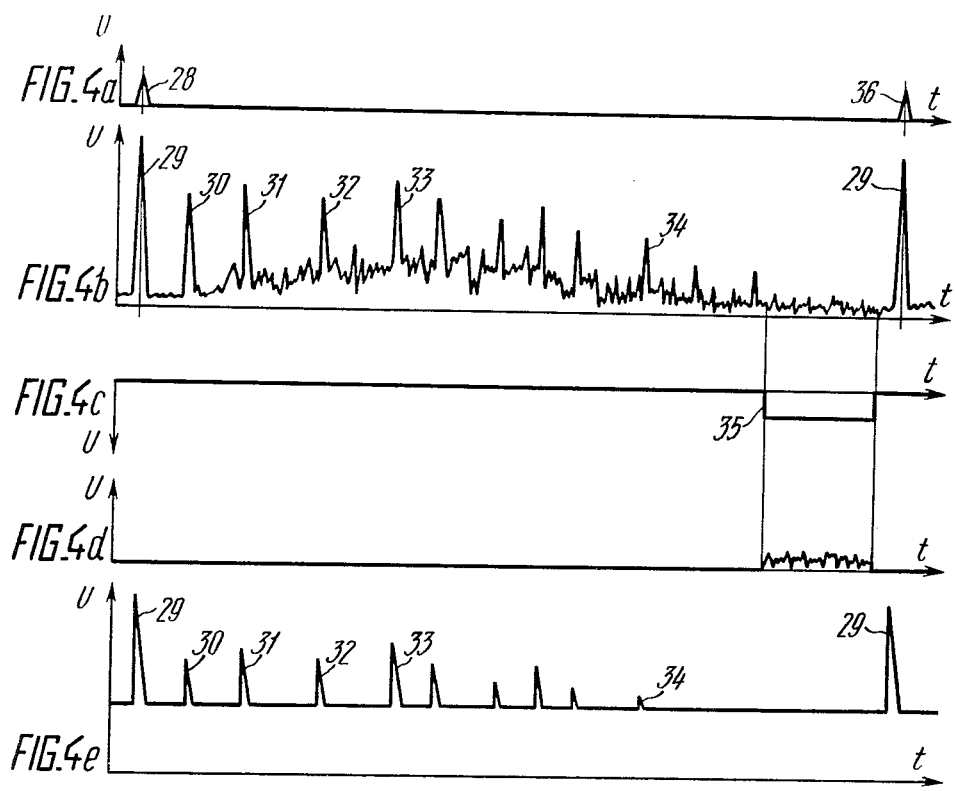

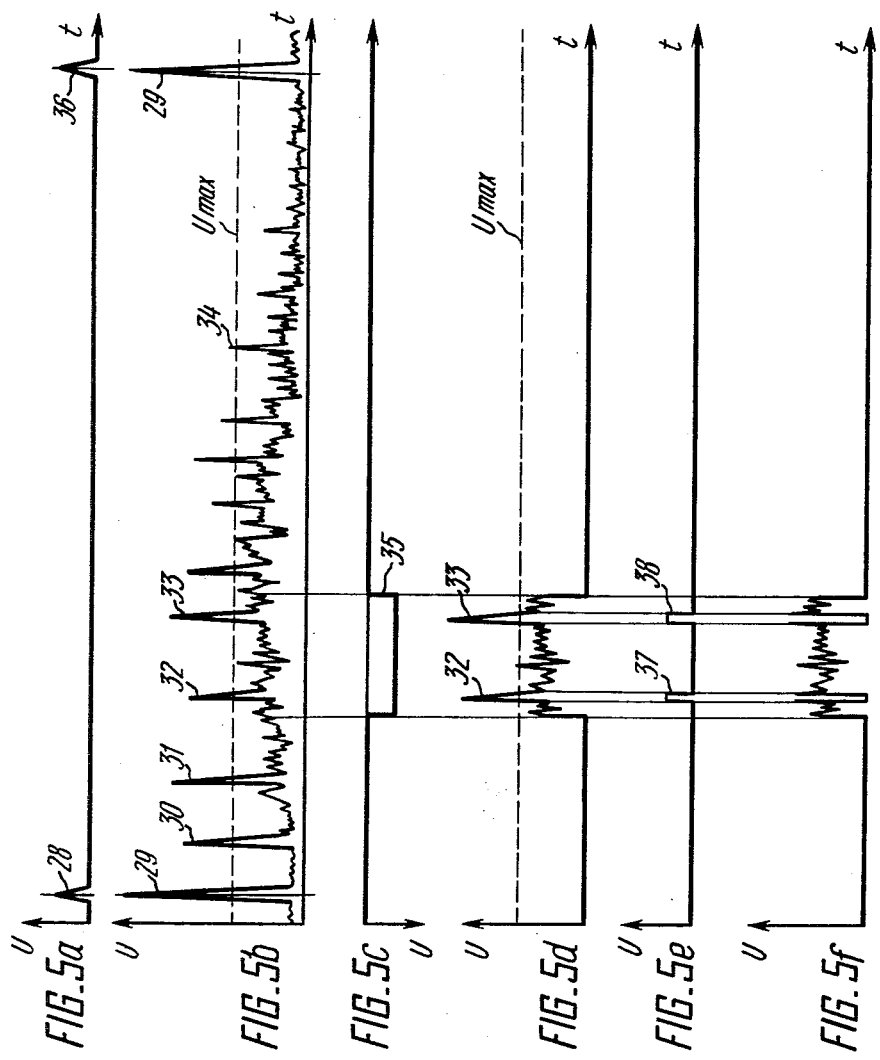

METHOD AND DEVICE FOR ULTRASONIC INSPECTION OF MATERIALS

FIELD OF THE INVENTION

The present invention relates to methods and means for nondestructive inspection of materials and, more particularly, to a method for ultrasonic inspection of materials and a device for carrying out that method.

The method and device according to the invention are chiefly applicable to ultrasonic inspection of materials and manufactured articles with a view to detecting local defects in products of the metallurgical, machine-building and aviation industries and in power engineering. The invention is further applicable to information and measuring instruments and systems where pulse signals are used as information carriers.

BACKGROUND OF THE INVENTION

There is known a method for ultrasonic inspection of materials (cf. A. K. Gurvich, I. N. Yermolov, "Ultrazvukovoy control svarnykh shvov"/"Ultrasonic Inspection of Welded Joints"/, Technika Publishers, Kiev, 1972, pp. 66–69), which comprises emitting ultrasonic vibrations into a material, receiving and processing the reflected ultrasonic vibrations, setting a noise cut-off level, separating signals from noise at a preset level and recording the results of the inspection. According to the method under review, the noise cut-off level is set manually by the operator who observes the noise level in the maximum sensitivity zone.

There is known a device for effecting the method under review, wherein the output of an ultrasonic generator, whose input is connected to one of the outputs of a synchronizer, is connected to the input of an ultrasonic transducer which is acoustically coupled to a material to be inspected; the output of the ultrasonic transducer is electrically coupled via a unit for receiving and processing reflected ultrasonic vibrations and a unit for separating signals from noise, which are placed in series, to a first input of a signals recording unit whose second input is connected to a second output of the synchronizer. In the device under review, the unit for separating signals from noise is a noise cut-off detector built around semiconductor diodes; the noise cut-off level is determined by the value of reference voltage which is set manually by the operator in accordance with the noise level in the material under inspection.

Noise levels may differ considerably even in adjacent areas of an article being tested, which is due to the structural non-uniformity of the material, as well as an inadequate acoustic contact.

Such situations often occur when inspecting articles of a complex shape and variable thickness, manufactured from some of the recently developed alloys with their varible structural noise levels. Reactors and pipelines of atomic power stations may serve as an example.

Manual setting of the noise cut-off level in the known device does not make it possible to rapidly change that level following a change in the noise level in the material being tested.

Furthermore, an optimum sensitivity is never reached because the operator normally sets the noise cut-off level at a point somewhat higher than the maximum noise level.

Due to the subjective selection of the noise cut-off level, this level may be higher than necessary; as a result, some flaws may remain undetected. The noise cut-off level may also be lower than necessary, which may lead to a detection of false defects. In both cases the inspection lacks confidence.

The rate of inspection of articles having portions with different structural noise levels is quite low because at each such portion one must readjust the noise cut-off level; if the structural noise level of a portion differs from that of the previous portion, the former portion must be inspected twice.

The device under review has to be readjusted each time it is used to inspect a different article with a significantly different structural noise level. However, such a readjustment is a complicated and arduous task.

SUMMARY OF THE INVENTION

It is an object of the present invention to carry out ultrasonic inspection so as to make it possible to rapidly change the noise cut-off level following a change in the noise level of the material being tested, which possesses different structural noise levels.

It is another object of the invention to increase the rate of ultrasonic inspection of materials.

It is still another object of the invention to increase the confidence of ultrasonic inspection of materials.

It is yet another object of the invention to ensure an optimum sensitivity in the course of ultrasonic inspection of materials.

The foregoing objects are attained by providing a method for ultrasonic inspection of materials, comprising emitting ultrasonic vibrations into a material, receiving and processing the reflected ultrasonic vibrations, setting a noise cut-off level in the maximum sensitivity zone, separating signals from noise at a preset level and recording the results of the inspection, which method is characterized, according to the invention, in that said noise cut-off level is automatically set for each period of radiating ultrasonic vibrations to be equal to the mean power noise per interval of time selected within the maximum sensitivity zone of a preceding period of radiating ultrasonic vibrations.

If the interval of time is selected in the region of signals against the background of noise, it is expedient that the setting of the noise cut-off level in that region should be preceded by time selection of the noise and thus separating signals from the noise at a known maximum noise level, and that the noise cut-off level should be set with reference to the separated noise level.

The objects of the present invention are further attained by providing a device for ultrasonic inspection of materials intended to carry out the above method, wherein an output of an ultrasonic generator whose inputs is connected to one of outputs of a synchronizer, is connected to an input of an ultrasonic transducer acoustically coupled to a material being tested, an output of the ultrasonic transducer being electrically coupled via a unit for receiving and processing reflected ultrasonic vibrations and a unit for separating signals from noise, that are placed in series, to a first input of a signals recroding unit whose second input is connected to a second output of the synchronizer, which device further comprises, according to the invention, a mean noise power measuring unit and a time selector including an AND gate and a gate pulse forming circuit whose input is connected to a third output of the synchronizer, whereas an output of said gate pulse forming circuit is connected to one of inputs of the AND gate whose other input is connected to an output of the unit for receiving and processing reflected signals, and output of the AND gate being electrically coupled to an input of the mean noise power measuring unit whose output is connected to a control input of the unit for separating signals from noise and to a third input of the signals recording unit.

It is desirable that the output of the AND gate should be directly connected to the input of the mean noise power measuring unit.

It is advisable that the time selector should be additionally provided with a second gate pulse forming circuit, its input being connected to the output of the AND gate, and with a NAND gate whose first input is electrically coupled to the output of the AND gate, a second input of the NAND gate being connected to an output of the second gate pulse forming circuit, an output of the NAND gate being connected to the input of the mean noise power measuring unit.

It is equally advisable that the time selector should further include a delay circuit to be electrically interposed between the output of the AND gate and the first input of the NAND gate.

The proposed method and device for ultrasonic inspection of materials make it possible to carry out ultrasonic inspection in such a way as to rapidly change the noise cut-off level following a change in the noise level of the material of an article possessing different structural noise levels.

The use of the method and device according to the invention accounts for an increased efficiency and a greater confidence of the inspection; the method and device of this invention also guarantee a maximum sensitivity.

BRIEF DESCRIPTION OF THE ACCOMPANYING DRAWINGS

Other objects and advantages of the present invention will become more apparent from the following detailed description of preferred embodiments thereof, taken in conjunction with the accompanying drawings, wherein.

Figure 1:
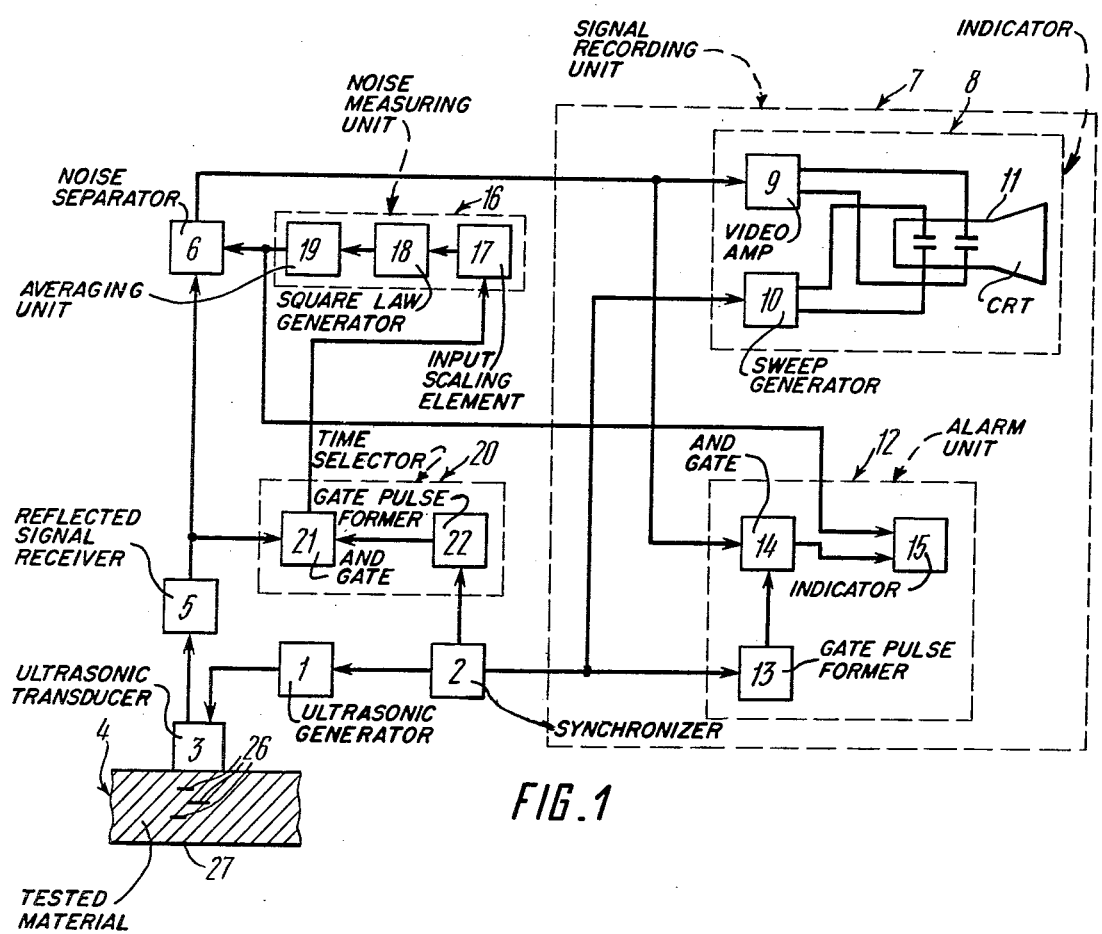
FIG. 1 is a block diagram of a device for ultrasonic inspection of materials in accordance with the invention, incorporating a first embodiment of the time selector.
Figure 2:
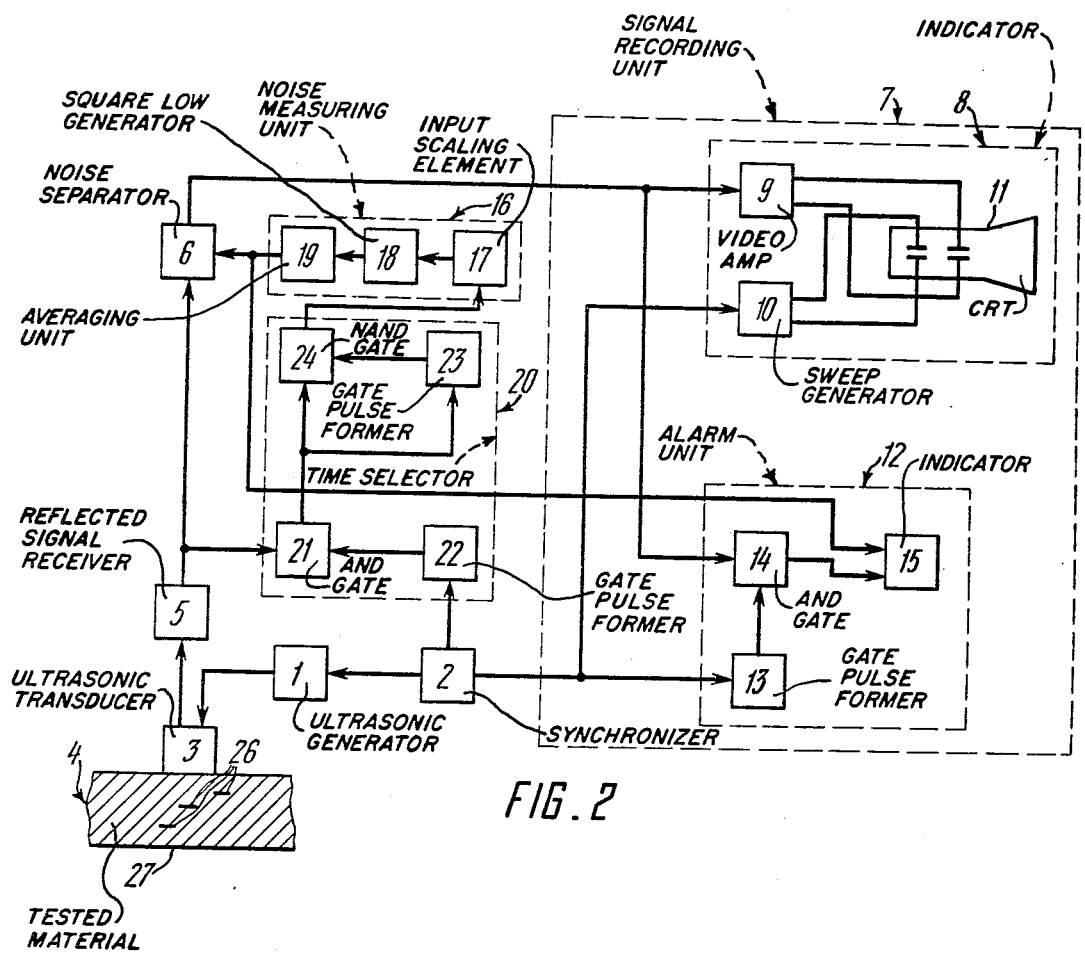
FIG. 2 is a block diagram of the device of FIG. 1, incorporating a second embodiment of the time selector.

FIGS. 4a, b, c, d, e are time plots of processes at different points of the device for ultrasonic inspection of materials of FIG. 1;

FIGS. 5a, b, c, d, e, f are time plots of processes at different points of the device for ultrasonic inspection of materials of FIG. 2.

DETAILED DESCRIPTION

The proposed method for ultrasonic inspection of materials is as follows.

Ultrasonic vibrations are sent into the material of an article being tested, which is followed by receiving vibrations reflected from defects and the bottom surface of the article. These vibrations are preprocessed (i.e. amplified and detected), and a noise cut-off level is automatically set for each period of radiating ultrasonic vibrations, which noise cut-off level is equal to the mean noise power over a certain interval of time.

The interval of time is selected within a maximum sensitivity zone of the period of radiating ultrasonic vibrations, which is either in a defect-free region or in a region of signals coming against the background of noise. These signals are a main bang and pulses reflected from flaws and the bottom surface of the article being tested. The defect-free region is a zone of a period of radiating ultrasonic vibrations, wherein the probability of occurrence of signals reflected from flaws is close to zero.

The setting of the noise cut-off level with reference to the noise level in the defect-free region is followed by separating signals from noise at that level and recording the results of the inspection.

If the interval of time for setting the noise cut-off level is selected within a region of signals against the background of noise, the setting of the noise cut-off level in that region is preceded by a time selection of noise from signals at a known maximum noise level, whereupon the noise cut-off level is set with reference to the level of the separated noise.

Signals are then separated from noise at that level, and the results of the inspection are recorded.

The foregoing method is carried out with the aid of a device for ultrasonic inspection of materials, comprising an ultrasonic generator 1 (FIG. 1) and a synchronizer 2 which is a conventional blocking generator with three outputs one of which is connected to an input of the ultrasonic generator 1.

The latter's output is connected to an input of an ultrasonic transducer 3 which is acoustically coupled to the material of an article 4 being tested, shown in section.

An output of the ultrasonic transducer 3 is electrically coupled via a unit 5 for receiving and processing reflected ultrasonic vibrations and a unit 6 for separating signals from noise, which are placed in series, to a first input of a signals recording unit 7. The unit 6 for separating signal from noise is a noise cut-off detector.

The unit 5 for receiving and processing reflected ultrasonic vibrations is a time gain control preamplifier. The signal recording unit 7 comprises an indication means 8 which includes a video amplifier 9 whose input is connected to an output of the unit 6 for separating signals from noise, a sweep generator 10 whose input is connected to the second output of the synchronizer 2, and a cathode-ray tube 11, its vertical-deflection plates and horizontal-deflection plates being connected to outputs of the video amplifier 9 and the sweep generator 10, respectively.

The signals recording unit 7 further includes an automatic flaw alarm unit 12 incorporating a gate pulse forming circuit 13 whose input is connected to the second output of the synchronizer 2, an AND gate 14, its first input being connected to an output of the gate pulse forming unit 13, whereas a second input of said AND gate 14 is connected to the output of the unit 6 for separating signals from noise, and an inspection result indicator 15 whose first input is connected to an output of the AND gate 14.

The inspection result indicator 15 incorporates an input threshold element with an adjustable trigger level.

The device according to the invention further includes a mean noise power measuring unit 16 which contains in series an input scaling element 17, a square-law generator 18 and an averaging unit 19. The device further includes a time selector 20 having an AND gate 21 and a gate pulse forming circuit 22 whose input is connected to the third output of the synchronizer 2.

An output of the gate pulse forming circuit 22 is connected to a first input of the AND gate 21 whose second input is connected to the output of the unit 5 for receiving and processing reflected ultrasonic vibrations.

An output of the AND gate 21 is connected to an input of the scaling element 17. An output of the averaging unit 19 is connected to a control input of the unit 6 for separating signals from noise and to a control input of the inspection result indicator 15.

Unlike the device of FIG. 1, the time selector 20 of the device shown in FIG. 2 additionally includes a second gate pulse forming circuit 23 (FIG. 2) whose input is connected to the output of the AND gate 21, and a NAND gate 24 whose first input is connected to the output of the AND gate 21, its second output being connected to an output of the second gate pulse forming circuit 23, whereas an output of said NAND gate 24 is connected to the input of the scaling element 17 of the mean noise power measuring unit 16.

Figure 3:
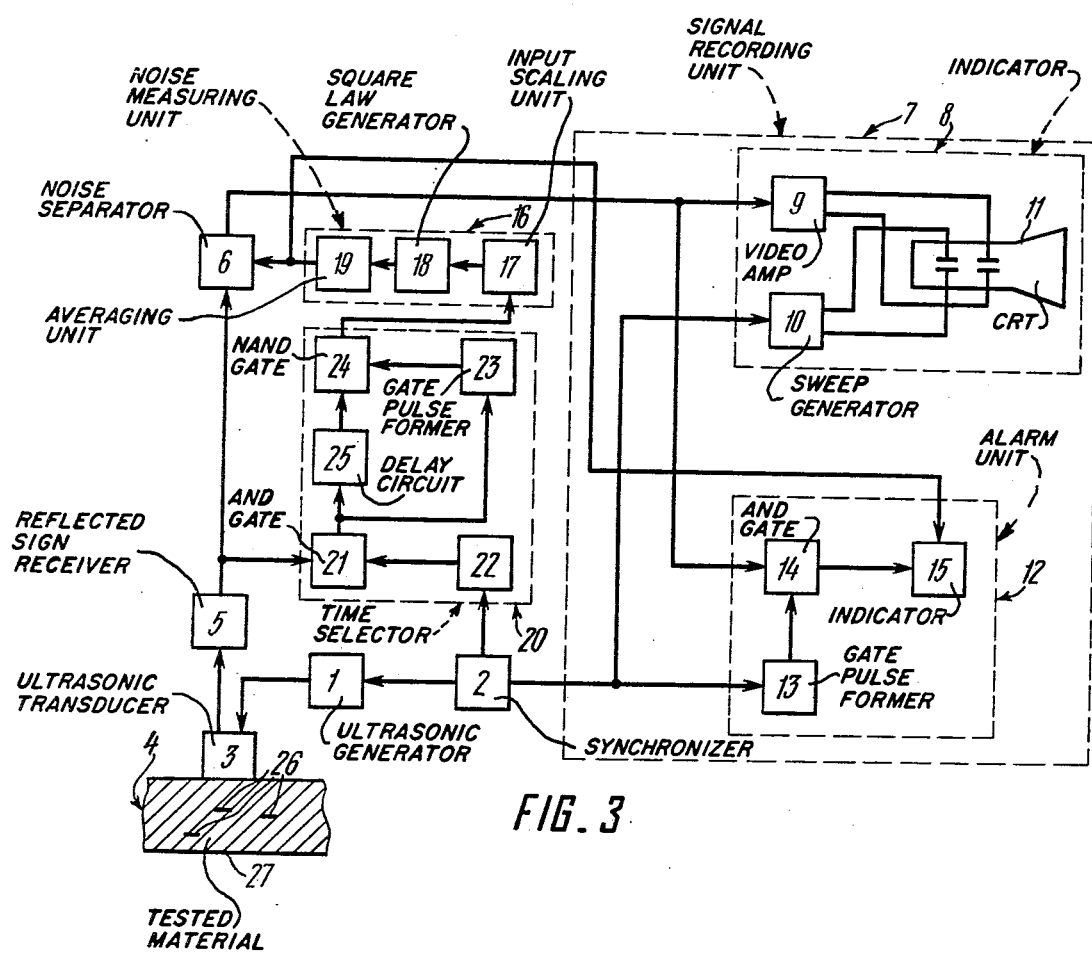
FIG. 3 is a block diagram of the device of FIG. 1, incorporating a third embodiment of the time selector.

Unlike the device of FIG. 2, the time selector 20 of the device shown in FIG. 3 further includes a delay circuit 25 electrically interposed between the output of the AND gate 21 and the first input of the NAND gate 24.

FIGS. 1, 2 and 3 conventionally show defects 26 and a bottom surface 27 of the article 4 being tested.

In FIG. 4:

FIG. 4a is a time plot of pulses 28 and 36 at the output of the synchronizer 2 (FIG. 1);

FIG. 4b is a time plot of pulse signals 29 (FIG. 4), 30, 31, 32, 33 and 34 against the background of noise at the output of the unit 5 (FIG. 1) for receiving and processing reflected ultrasonic vibrations;

FIG. 4c is a time plot of a gate pulse 35 (FIG. 4) at the output of the gate pulse forming circuit 22 (FIG. 1);

FIG. 4d is a time plot of noise discriminated at the output of the AND gate 21 (FIG. 1);

FIG. 4e is a time plot of the pulse signals 29 (FIG. 4), 30, 31, 32, 33 and 34 at the output of the unit 6 (FIG. 1) for separating signals from noise.

In FIG. 5:

FIG. 5a is a time plot of pulses 28 and 36 at the output of the synchronizer 2 (FIG. 2);

FIG. 5b is a time plot of the pulse signals 29 (FIG. 5), 30, 31, 32, 33 and 34 against the background of noise at the output of the unit 5 (FIG. 2) for receiving and processing reflected ultrasonic vibrations;

FIG. 5c is a time plot of the gate pulse 35 (FIG. 5) at the output of the gate pulse forming circuit 22 (FIG. 2);

FIG. 5d is a time plot of the pulse signals 32 (FIG. 5) and 33 against the background of noise at the output of the AND gate 21 (FIG. 2);

FIG. 5e is a time plot of gate pulses 37 and 38 at the output of the gate pulse forming circuit 23 (FIG. 2);

FIG. 5f is a time plot of noise separated from the signals 32 (FIG. 5) and 33 at the output of the NAND gate 24 (FIG. 2).

The proposed device for ultrasonic inspection of materials operates as follows.

The first pulse 28 (FIG. 4, plot a) of the synchronizer 2 (FIG. 1) triggers the sweep generator 10, the gate pulse forming circuits 13 and 22 and the ultrasonic generator 1 which excites the ultrasonic transducer 3. The latter converts electrical ultrasonic vibrations to mechanical vibrations which propagate in the material of the article 4 being tested due to the acoustic contact between the surface of the ultrasonic transducer 3 and that of the article 4.

The elastic vibrations that are reflected from the defects 26 and the bottom surface 27 of the article 4 are applied to the ultrasonic transducer 3 which converts them to electric signals.

These signals are simultaneously applied via the unit 5 for receiving and processing reflected ultrasonic vibrations to the input of the unit 6 for separating signals from noise and the input of the AND gate 21 of the time selector 20. At the ouput of the unit 5 for receiving and processing reflected ultrasonic vibrations the following signals are produced against the background of noise: the pulse signal 29 (FIG. 4, plot b) corresponding to the moment the ultrasonic vibrations and radiated into the material (the main bang); the pulse signals 30, 31 and 32 reflected from the flaws 26 (FIG. 1) of the article 4 being tested; and the pulse signals 33 and 34 (FIG. 4, plot b) reflected from the bottom surface 27 (FIG. 1) of the article 4.

The gate pulse forming circuit 22 produces the pulse 35 (FIG. 4, plot c) whose duration is equal to the time interval during which the mean noise power is determined; the time position of said pulse 35 is selected in the maximum sensitivity zone of the defect-free region.

The gate pulse forming circuit 22 (FIG. 1) produces the pulse 35 (FIG. 4, plot c) at the end of the period of radiating ultrasonic vibrations, which period ends up with the pulse 36 (FIG. 4, plot a) of the synchronizer 2 (FIG. 1).

The gate pulse 35 (FIG. 4, plot c) is applied to the second input of the AND circuit 21 (FIG. 1); as this takes place, noise is applied to the first input of said AND gate 21.

The AND gate 21 is driven into conduction so that the discriminated noise (FIG. 4, plot d) is applied to the input of the mean noise power measuring unit 16 (FIG. 1).

The measuring unit 16 converts the noise to d.c. voltage proportional to the mean noise power over the interval of time corresponding to the duration of the pulse 35 (FIG. 4, plot c).

The d.c. voltage is further applied to the input of the unit 6 (FIG. 1) for separating signals from noise and to the input of the inspection result indicator 15.

During the next radiation period, the unit 6 separates the pulse signals 29 (FIG. 4, plot e), 30, 31, 32, 33 and 34 from noise at a preset level determined by the d.c. voltage.

The disciminated pulse signals 29, 30, 31, 32, 33 and 34 are applied from the output of the unit 6 (FIG. 1) for separating signals from noise via the video amplifier 9 to the vertical-dflection plates of the cathode-ray tube 11; meanwhile, sweep voltage is applied to the horizontal-deflection plates of said cathode-ray tube 11.

The gate pulse forming unit 13 of the automatic flaw alarm unit 12 forms, under the action of the synchronizer 2, a gate pulse which sets the inspection zone at an output of the AND gate 14.

The inspection result indicator 15 makes use of light, audio or relay signalling means to indicate flaws, which is effected with an optimum sensitivity set by the d.c. output voltage of the mean noise power measuring unit 16. This d.c. voltage determines the trigger level of the inspection result indicator 15.

The output signals of the inspection result indicator 15 may also be sent to auxiliary peripheral data processing devices, for example, a computer.

During each next period of radiation of ultrasonic vibrations, the foregoing sequence of events is repeated.

Thus from period to period, the process of inspection is regularly accompanied by an automatic monitoring of the noise level of reflected ultrasonic vibrations.

In the defect-free region of the period of radiation of ultrasonic vibrations, structural, reverberation and acoustic noise is reduced to a level of noise which is due to other factors; thus the above-mentioned types of noise are not taken into account when forming d.c. voltage which controls the noise cut-off level.

In many cases the level of the foregoing noise components in the zone of inspection may be much greater than the level of noise due to other factors, such as selfnoise or externally induced noise; this is especially so when testing articles of complex shapes manufactured from up-to-date alloys.

In contrast to the case of FIG. 1, the accuracy of setting the noise cut-off level is improved by selecting the time position of the gate pulse 35 (FIG. 5, plot c) formed by the circuit 22 (FIG. 2) in the region of the signals 29 (FIG. 5, plot b), 30, 31, 32, 33 and 34 against the background of noise.

In the case under review, this time position is selected on the inspection zone.

During an interval of time corresponding to the diration of the pulse 35 (FIG. 5, plot c), the AND gate 21 (FIG. 2) passes the pulse signals 32 (FIG. 5, plot d) and 33 against the background of noise to the inputs of the gate pulse forming circuit 23 (FIG. 2) and the NAND gate 24.

The operation threshold of the gate pulse forming circuit 23 corresponds to a maximum noise level $U_{max}$ (FIG. 5, plot d) for the given conditions.

Under the action of the pulse signals 32 and 33, the circuit 23 (FIG. 2) produces the gate pulses 37 (FIG. 5, plot e) and 38 whose durations and positions in time correspond to those of the pulse signals 32 (FIG. 5, plot d) and 33 at the $U_{max}$ level.

The NAND gate 24 (FIG. 2) carries out time selection of noise from the signals 32 (FIG. 5, plot d) and 33.

From the output of the NAND gate 24 (FIG. 2), the discriminated noise (FIG. 5, plot f) is applied to the input of the mean noise power measuring unit 16 (FIG. 2), whereupon the inspection process proceeds as described above.

The delay circuit 25 (FIG. 3) compensates for the delay of the gate pulses 37 (FIG. 5, plot e) and 38 occurring in the gate pulse forming circuit 23 (FIG. 3); this accounts for a greater accuracy of time selection of noise from signals.

What is claimed is:

1. A method for ultrasonic inspection of materials, comprising: radiating ultrasonic vibrations into a material being tested; receiving and processing the reflected ultrasonic vibrations; automatically setting a noise cut-off level for each period of radiation of ultrasonic vibrations, which level is equal to the mean power of said noise over an interval of time selected within the maximum sensitivity zone of a preceding period of radiation of ultrasonic vibrations;

separating signals from noise at said preset level; and recording the results of the inspection.

2. A method as claimed in claim 1, whereby said automatic setting of the noise cut-off level is preceded by a time selection of said noise from signals within the region of signals against the background of noise, within a preselected interval of time and at a known maximum noise level, whereupon the noise cut-off level is automatically set with reference to the discriminated noise level, which noise cut-off level is equal to the mean noise power over a time interval selected within the maximum sensitivity zone of said period of radiation of ultrasonic vibrations in the region of signals against the background of noise.

3. A device for ultrasonic inspection of materials by separating signals from noise at a noise cut-off level which is automatically set for each period of radiation of ultrasonic vibrations, the noise cut-off level being equal to the mean noise power over a preselected interval of time, which device comprises:

an ultrasonic generator;

an ultrasonic transducer acoustically coupled to a material being tested, its input being connected to an output of said ultrasonic generator;

a unit for receiving and processing reflected ultrasonic vibrations, its input being connected to an output of said ultrasonic transducer;

a unit for separating signals from noise, its input being connected to an output of said unit for receiving and processing reflected ultrasonic vibrations;

a signal recording unit, its first input being connected to an output of said unit for separating signals from noise;

a synchronizer, its first output being connected to an input of said ultrasonic generator, its second output being connected to a second input of said signal recording unit;

a mean noise power measuring unit, its output being connected to a control input of said unit for separating signals from noise and to a third input of said signal recording unit;

a time selector;

an AND gate of said time selector, its first input being connected to the output of said unit for receiving and processing reflected ultrasonic vibrations, an output of said AND gate being electrically coupled to an input of said mean noise power measuring unit; and a gate pulse forming circuit of said time selector, its input being connected to a third output of said synchronizer, while an output of said gate pulse forming circuit is connected to a second input of said AND gate.

4. A device as claimed in claim 3, wherein the output of said AND gate of said time selector is directly connected to the input of said mean noise power measuring unit.

5. A device as claimed in claim 3, comprising:

a second gate pulse forming circuit of said time selector, its input being connected to the output of said AND gate;

a NAND gate of said time selector, its first input being electrically coupled to the output of said AND gate, a second input of said NAND gate being connected to the output of said second gate pulse forming circuit, whereas an output of said NAND gate is connected to the input of said mean noise power measuring unit.

6. A device as claimed in claim 5, comprising:

a delay circuit of said time selector, interposed between the output of said AND gate and said first input of said NAND gate.

* * * * *